(12) United States Patent
Ertas et al.

(10) Patent No.: US 8,162,822 B2
(45) Date of Patent: Apr. 24, 2012

(54) ENDOSCOPY DEVICE WITH INTEGRATED RFID AND EXTERNAL NETWORK CAPABILITY

(75) Inventors: Hasan Ertas, Sunnyvale, CA (US);
Ruzbeh Shariff, Santa Clara, CA (US);
Sohail Desai, Campbell, CA (US);
Brannon P. Wells, San Jose, CA (US);
Rajeshwari Srinivasan, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 13/068,440

(22) Filed: May 11, 2011

(65) Prior Publication Data

US 2011/0219125 A1 Sep. 8, 2011

Related U.S. Application Data

(60) Division of application No. 11/342,474, filed on Jan. 30, 2006, now Pat. No. 7,976,461, which is a continuation of application No. 10/778,274, filed on Feb. 12, 2004, now abandoned.

(51) Int. Cl.
*A61B 1/04* (2006.01)
(52) U.S. Cl. .......................... 600/118; 600/101; 600/178
(58) Field of Classification Search ...... 606/1; 600/101, 600/118, 178
See application file for complete search history.

(56) References Cited

U.S. PATENT DOCUMENTS

| | | | |
|---|---|---|---|
| 5,651,780 | A | 7/1997 | Jackson et al. |
| 5,821,854 | A | 10/1998 | Dorinski et al. |
| 6,490,490 | B1 | 12/2002 | Uchikubo et al. |
| 6,697,764 | B2 | 2/2004 | Corby, Jr. et al. |
| 6,861,954 | B2 | 3/2005 | Levin |
| 7,154,378 | B1 | 12/2006 | Ertas et al. |
| 7,498,950 | B1 | 3/2009 | Ertas et al. |
| 2001/0051766 | A1 | 12/2001 | Gazdzinski |
| 2003/0060682 | A1 | 3/2003 | Handa et al. |
| 2003/0097042 | A1 | 5/2003 | Eino |
| 2003/0100294 | A1 | 5/2003 | Hosono |
| 2003/0174205 | A1 | 9/2003 | Ambling et al. |
| 2003/0182584 | A1 | 9/2003 | Banes et al. |
| 2003/0204724 | A1 | 10/2003 | Ayyagari et al. |
| 2005/0096684 | A1 | 5/2005 | Farrow et al. |

*Primary Examiner* — Matthew J Kasztejna
(74) *Attorney, Agent, or Firm* — Flynn, Thiel, Boutell & Tanis, P.C.

(57) ABSTRACT

A unit of equipment designed for use in endoscopic surgery includes radio frequency identification (RFID) circuitry and a network interface. The RFID circuitry can be used to store information of various types, such as component usage tracking information, user preferences, usage logs, error logs, device settings, etc. The network interface allows the unit to communicate over an external network with a remote server. Information, such as information stored in the RFID circuitry or in a separate memory, may be sent over the network to a desired destination, such as a server operated by the manufacturer of the equipment.

20 Claims, 9 Drawing Sheets

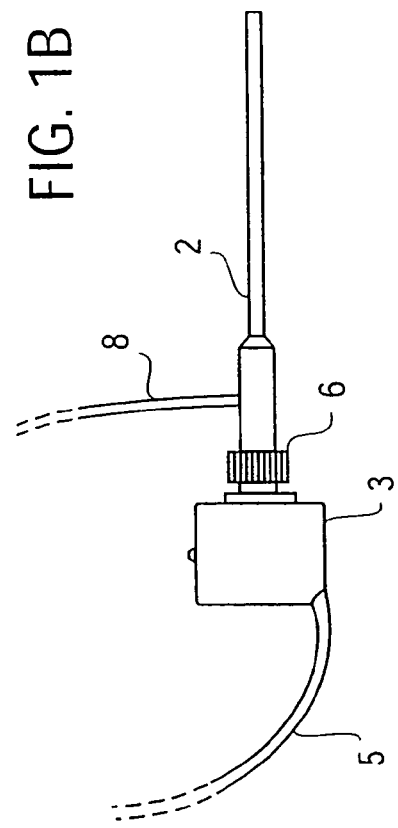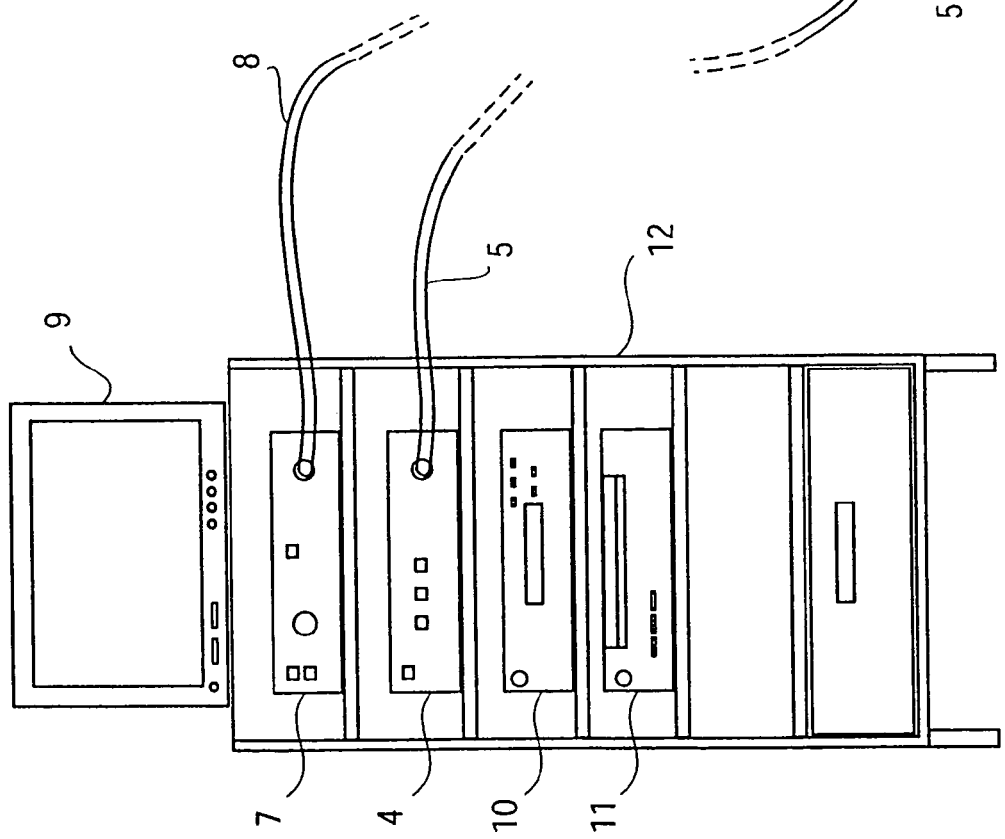

ENDOSCOPY DEVICE WITH INTEGRATED RFID AND EXTERNAL NETWORK CAPABILITY

CROSS REFERENCE TO RELATED APPLICATIONS

This is a divisional application of prior U.S. application Ser. No. 11/342,474, filed Jan. 30, 2006, which issued as U.S. Pat. No. 7,976,461, which is a continuation of prior U.S. application Ser. No. 10/778,274, filed Feb. 12, 2004, now abandoned, the disclosures of which are hereby incorporated by reference.

FIELD OF THE INVENTION

The present invention pertains to endoscopy equipment, and more particularly, to an endoscopy device with integrated RFID and external network capability.

BACKGROUND

Endoscopy in the medical field allows internal features of the body of a patient to be viewed without the use of traditional, fully-invasive surgery. FIGS. 1A and 1B collectively illustrate an endoscopic imaging system such as commonly used in the medical field. FIG. 1A generally illustrates the image generation and display components of the system, while FIG. 1B illustrates the data acquisition components of the system. FIG. 1B shows the data acquisition components, which include an endoscope 2, a camera 3, and a coupler 6 connecting the endoscope 2 to the camera 3. The camera 3 acquires color video image data of internal features of a body through a system of lenses in the endoscope 2. FIG. 1A shows the image generation and display components of the system, which include a camera control unit (CCU) 4, a light source unit 7, a monitor 9, and various other devices 10 and 11, which are stored on a mobile cart 12. The other devices 10 and 11 may include, for example, a video recorder, a printer, an RF cutter console to control an RF cutter during endoscopic surgery, and/or a shaver console to control a shaver during endoscopic surgery. Various other system configurations are also possible.

High-intensity light is provided to the endoscope 2 by the light source unit 7 through a flexible light conduit 8, such as fiber optic cable. Operation of the camera system can be controlled from the CCU 4. The camera 3 is coupled to the camera control unit (CCU) 4 by a flexible transmission line 5. The transmission line 5 conveys power to the camera 3, video image data from the camera 3 to the CCU 4, and various control signals bi-directionally between the camera 3 and the CCU 4. Image data received by the CCU 4 from the camera 3 are processed and converted to video images by the CCU 4, which are displayed on the monitor 9, and if desired, recorded by a video recorder and/or used to generate static images that can be printed by a printer.

Light from the light source unit 7 is generated by a replaceable light bulb (not shown in FIG. 1) inside the light source unit 7. The light bulb has a limited lifetime, i.e., eventually it will fail. It is extremely undesirable for the light bulb to fail during surgery, due to the potential danger to the patient posed by a sudden loss of illumination or a delay in surgery to replace the bulb, the risk of explosion of the bulb, and other potential adverse consequences. Therefore, it is necessary to replace the light bulb before a failure occurs.

After a number of hours of use, which can be predicted with reasonable accuracy, the likelihood of failure of the light bulb increases substantially. This number of hours may be considered to be the light bulb's maximum useful lifetime. The manufacturer of the light bulb or the light source unit typically specifies the useful lifetime and/or a warranty period of the light bulb, in terms of hours of use. The manufacturer may offer an incentive to the user (customer) to replace the light bulb prior to expiration of the warranty period and/or the useful lifetime.

However, it is burdensome for users to keep track of the number of hours the light bulb has been used. The light bulb cannot inherently track the number of hours that it has been used, as it lacks any circuitry to do so. Physical limitations that hinder access to low voltage levels on the light bulb generally prevent the use of any conductively powered circuitry to perform this task.

At least one known design for a light source unit attempts to address this problem. The light source unit keeps track of bulb use on its own, without actually knowing the true cumulative use of the bulb, and provides a bulb hours display on the front panel of the light source unit. In this design, the user has to reset the bulb hours display whenever the bulb is replaced. Also, if the user replaces the bulb with a used bulb, the light source unit has no way of knowing this, and there is no way to cause the light source unit to accurately display the true hours of use of the replacement bulb.

Another problem associated with endoscopy light sources and other endoscopy equipment is that the manufacturer of the equipment may desire improved ability to predict, identify, or diagnose faults or failures in the equipment and to monitor device settings (e.g., for purposes~ of verifying proper usage of the equipment and/or assisting customers in using the equipment). To accomplish this, the manufacturer needs to continually have certain up-to-date data regarding the use and or performance of the equipment. However, once the equipment is deployed in the field, the manufacturer has very limited ability to obtain such information, typically either relying on the customer to provide the information or sending a sales or technical support representative to the customer premises.

BRIEF DESCRIPTION OF THE DRAWINGS

One or more embodiments of the present invention are illustrated by way of example and not limitation in the figures of the accompanying drawings, in which like references indicate similar elements and in which:

FIG. 1 illustrates an endoscopic imaging system;

DETAILED DESCRIPTION

Figure 2:
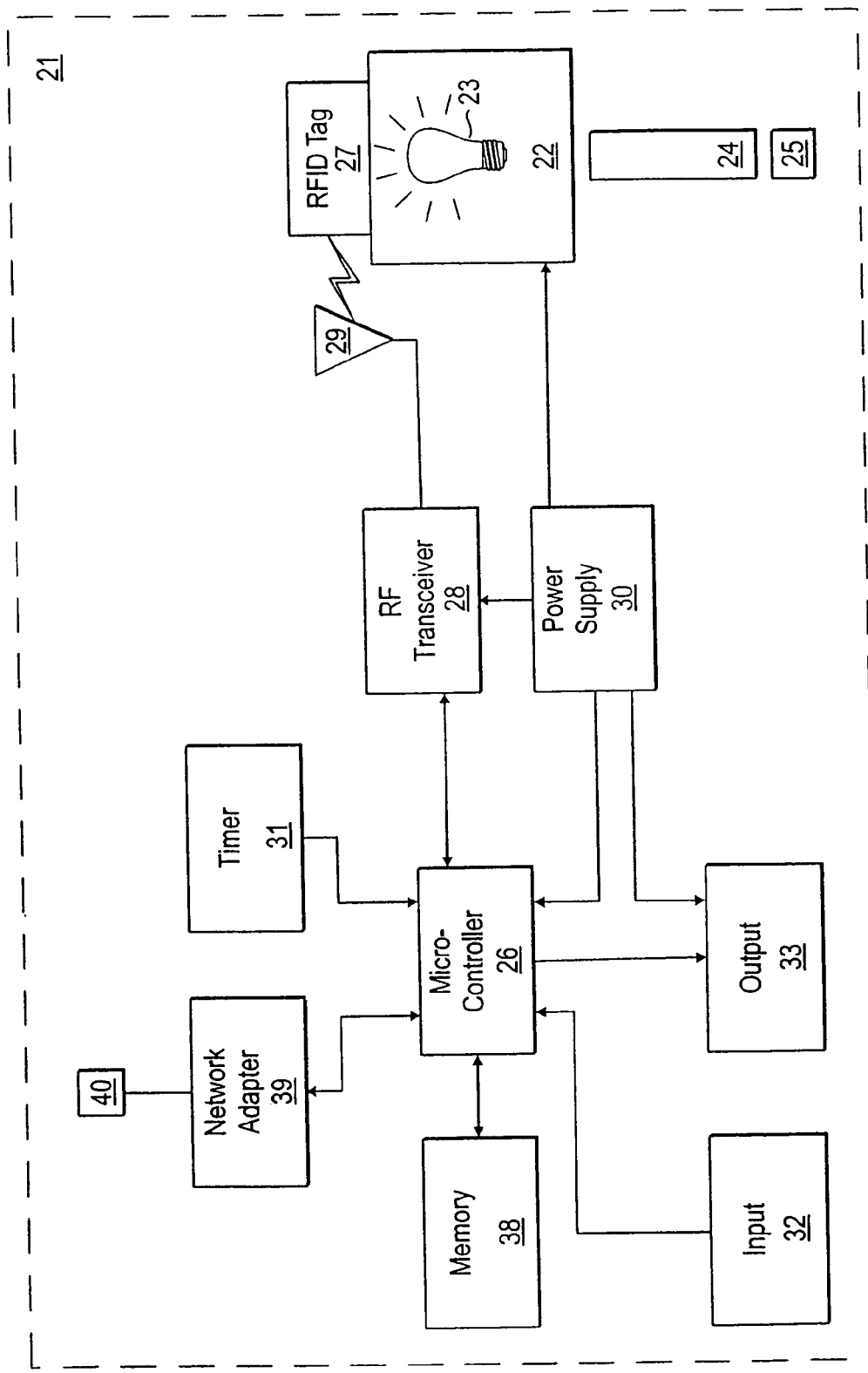
FIG. 2 is a block diagram of a light source unit for use in an endoscopic camera system.

A method and apparatus to enable an endoscopy device with integral RFID capability to communicate with a remote server over a network are described. Note that in this description, references to "one embodiment" or "an embodiment" mean that the feature being referred to is included in at least one embodiment of the present invention. Further, separate references to "one embodiment" or "an embodiment" in this description do not necessarily refer to the same embodiment; however, such embodiments are also not mutually exclusive unless so stated, and except as will be readily apparent to those skilled in the art from the description. For example, a feature, structure, act, etc. described in one embodiment may also be included in other embodiments. Thus, the present invention can include a variety of combinations and/or integrations of the embodiments described herein.

In accordance with the invention, radio frequency identification (RFID) circuitry is used inside a unit of equipment designed for use in endoscopic surgery. The unit also has a network interface to allow the unit to communicate over an external network with a remote server. The RFID circuitry can be used to store component usage information, which enables accurate tracking of use of a component independently of the particular unit in which the component is used. In addition, the RFID circuitry can be used to store other types of information, such as device settings, user preferences, usage logs, and error or failure data. The network connection can be used to send such data to the manufacturer of the equipment, along with other data if desired.

To facilitate description, it is henceforth assumed herein that the unit of equipment is a light source unit for providing light for use by endoscopic camera, and that the light source is a light bulb. In other embodiments, however, the light source may be something other than a light bulb, such as one or more light-emitting diodes (LEDs), for example. Also, in other embodiments the unit of equipment may be something other than a light source unit, such as an endoscopic camera control unit (CCU), an RF cutter console to control an RF cutter during endoscopic surgery, a shaver console to control a shaver during endoscopic surgery, or a footswitch console containing foot-operated switches to control the functionality of other endoscopic devices during endoscopic surgery.

An inductively powered wireless RFID tag is affixed to an assembly containing the light bulb or other type of light source in the light source unit. The RFID tag on the light bulb assembly communicates with a conductively-powered radio frequency (RF) transceiver in the light source unit via a low-frequency modulation wave through the air (i.e., wirelessly). The RFID tag includes non-volatile memory, such as flash or some form of EPROM. The memory in the RFID tag is used to store (among other possible data) a value representing the cumulative duration of use of the light bulb.

The value is initially set by the manufacturer of the light bulb assembly. When the light bulb assembly is installed in the light source unit and the light source unit is powered on, the transceiver reads the value from the RFID tag and communicates the value to control circuitry in the light source unit. The control circuitry tracks use of the light bulb within the light source unit, and based on such tracking, periodically causes the transceiver to update the stored value in the RFID tag via the wireless link. Cumulative bulb usage hours is displayed on the front panel of the light source unit based on the current value stored in the RFID tag.

The RFID tag is powered by the same modulation wave that is used for communication between the transceiver and the RFID tag. Wireless communication between the transceiver and the RFID tag is achieved using an LC resonance circuit driven by the transceiver, which inductively couples with a corresponding LC resonance circuit within the RFID tag.

This approach enables accurate tracking of cumulative light bulb use, independently of the light source unit in which the bulb is used. The user never needs to reset the bulb usage display when the bulb is replaced. Hence, users are enabled to order and install replacement bulbs before they exceed the warranty period or fail unexpectedly. Furthermore, this approach enables the bulb usage display to remain accurate even if the light bulb is replaced by a used bulb.

This design also requires no direct contact between the RFID tag and either the antenna or the transceiver. The RFID tag also (or alternatively) may store various other types of data, such as a custom password that protects the system from external interruptions or intrusions, as well as other information.

As described further below, the light source unit also includes a network interface to allow the unit to communicate over an external network with a remote server operated by the manufacturer. The network connection allows various types of up-to-date information on the light source unit to be uploaded to the manufacturer, such as light bulb hours, usage logs and error logs, etc., to provide the manufacturer with better ability to predict, diagnose and correct problems with the light source unit, and to assist customers in using the unit. The network connection also allows software upgrades to be easily downloaded to the light source unit when they become available.

Note that the approach introduced herein is not limited in application to use with a light bulb or any other component of a light source unit. The approach introduced herein can be used to provide accurate tracking of cumulative use or other information associated with potentially any component in any piece of equipment. To facilitate explanation of the invention, however, the description which follows is directed to tracking use of a light bulb (or other light source) in a light source unit for use in endoscopy.

FIG. 2 is a block diagram showing the components of a light source unit 21 for use in an endoscopic imaging system. Light source unit 21 may be used in the same manner as light source unit 7 in FIG. 1. The light source unit 21 includes a light bulb assembly 22, which includes a light bulb 23 to generate high-intensity light to be transmitted through an endoscope. In other embodiments, the light bulb 23 may be replaced by another form of light source, such as one or more light-emitting diodes (LEDs), for example. The light source unit 21 further includes an internal light coupler 24 optically coupled to the light bulb 23 and to an external light conduit connector 25 on the front plate of the light source unit 21. During operation, light from the light bulb 23 is transmitted through the internal light coupler 24 and the light conduit connector 25 to a flexible light conduit such as fiber-optic cable (not shown in FIG. 2) connected externally to the light source unit 21, the opposite end of which is optically coupled to the endoscope.

The light source unit 21 further includes a microcontroller 26, an RFID tag 27, an RF transceiver 28, an antenna 29, a power supply 30, a timer 31, one or more input devices 32, and one or more output devices 33, memory 38, a network adapter 39, and an external network connector 40. The light source unit 21 may also contain components that are not shown or described, which are not germane to the present invention.

The microcontroller controls and coordinates the overall operation of the light source unit 21 by executing instructions stored in memory 38. The microcontroller may also include its own internal memory (not shown). Memory 38 is used to store both software and data and may represent multiple physical memory devices.

The network adapter 39 is used to provide bidirectional data communication with one or more remote processing systems via one or more networks. As described further below, the external network(s) over which the network adapter 39 communicates may include the Internet or other type of wide area network (WAN), a local area network (LAN), a corporate intranet, or any other type of network, or a combination of such networks. The network adapter 39 may be, for example, an Ethernet adapter, i.e., an adapter which communicates over the external network(s) using some form of Ethernet protocol. In certain embodiments, network adapter 39 may provide for wireless communication over the external network(s), such as wireless Ethernet. In other embodiments, the network adapter 39 may implement a different type of protocol for external data communication, such as Bluetooth, infrared (IR), etc.

In certain embodiments the network adapter 39 uses the RS-232 protocol to communicate with the microcontroller 26. External connection to the network adapter 39 is provided by external connector 40, which may be, for example, a standard RJ-45 connector in the case where Ethernet is used.

The input devices 32 may include, for example, one or more switches, buttons, or other devices, to control various functions of the light source unit 21, such as power on/off, mode selection, light intensity, etc. The output devices 33 are used to provide the user with information to facilitate operation of the light source unit 21, including cumulative usage hours of the light bulb 23, as well as feedback on parameters such as light intensity, etc. The output devices 33 may include one or more display devices, such as a liquid crystal display (LCD), cathode ray tube (CRT), plasma display, high definition television (HDTV) display, or the like, and/or one or more sound output devices (e.g., audio speakers). Furthermore, although the input devices 32 and output devices 33 are shown as being separate, an input device 32 and an output device 33 may be combined in a single device, such as a touchscreen display.

All of the active components shown in FIG. 2 except the RFID tag 27 are conductively powered by the power supply 30. The RFID tag 27 is powered by RF induction from the antenna 29.

Figure 3:
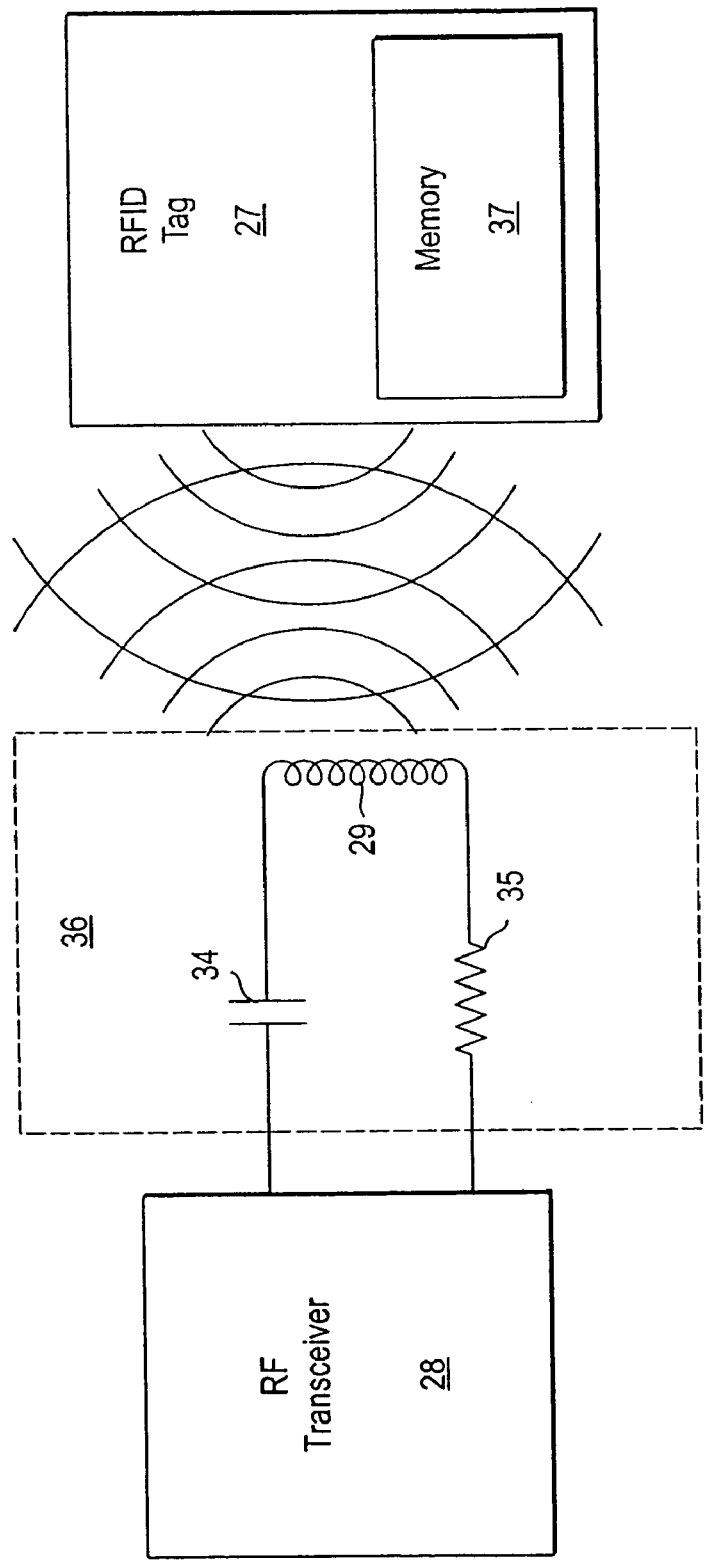
FIG. 3 shows a portion of a light source unit that relates to communication with an RFID tag.

In certain embodiments, the antenna 29 is a simple coil (i.e., an inductor) that forms part of a series LC resonance circuit, which is shown in FIG. 3. As can be seen from FIG. 3, the LC resonance circuit 36 is driven by the RF transceiver 28. The LC resonance circuit 36 includes the antenna (coil) 29, a capacitor 34, and a resistor 35, all coupled in series with the signal output of the RF transceiver 28. The antenna 29 inductively couples with a corresponding LC resonance circuit (not shown) within the RFID tag 27. The purpose of the resonance circuit 36 is to increase the size of the sinusoidal wave across the antenna 29, as discussed further below.

The resulting large-scale voltage wave produced at the antenna 29 charges a small capacitor that is attached to the resonance circuit in the RFID tag 27, provided the RFID tag 27 is positioned close to the antenna 29 (e.g., within about one inch, for the embodiments described herein). The small capacitor in the RFID tag 27 is used to drive the circuitry within the RFID tag 27 for a short period of time, i.e., as long as the charge remains on the small capacitor. Once the capacitor in the RFID tag 27 is charged and the RFID tag 27 is operating, the large-scale voltage wave is pulse amplitude modulated to provide communication between the RF transceiver 28 and the RFID tag 27.

The LC resonance circuit 36 is designed so that its natural resonant frequency is substantially equal to the frequency of the sinusoidal wave produced by the RF transceiver 28, subject to minor tuning. In general, the natural resonant frequency, $f_r$, of a series LC circuit is defined as $f_r = 1/(2\pi\sqrt{(LC)})$. Thus, in the embodiment discussed above, L in the foregoing formula is the inductance value of the antenna 29, and C is the capacitance value of the capacitor 34. In practice, this frequency varies due to factors such as the mutual inductance created by the coupling of the secondary coil in the RFID tag (not shown), and the variation in the values of the antenna 29 and capacitor 34. Therefore, for optimum results, the inductance and capacitance values of the antenna 29 and capacitor 34, respectively, should be tuned by measuring secondary power across the load at different frequencies around the calculated natural resonant frequency for the specific application load.

In one embodiment, the RF transceiver 28 transmits a 50-100 V peak-to-peak sinusoidal wave at a frequency of about 125 kHz; the capacitor 34 has a capacitance value of about 3.6 nanofarads; the antenna 29 has an inductance value of about 447 microhenries; and the resistor 35 has a resistance value of about 22 ohms. The antenna 29 is mounted within the light source unit 21 so that its center it is about one inch from the center of the RFID tag 27.

Figure 4:
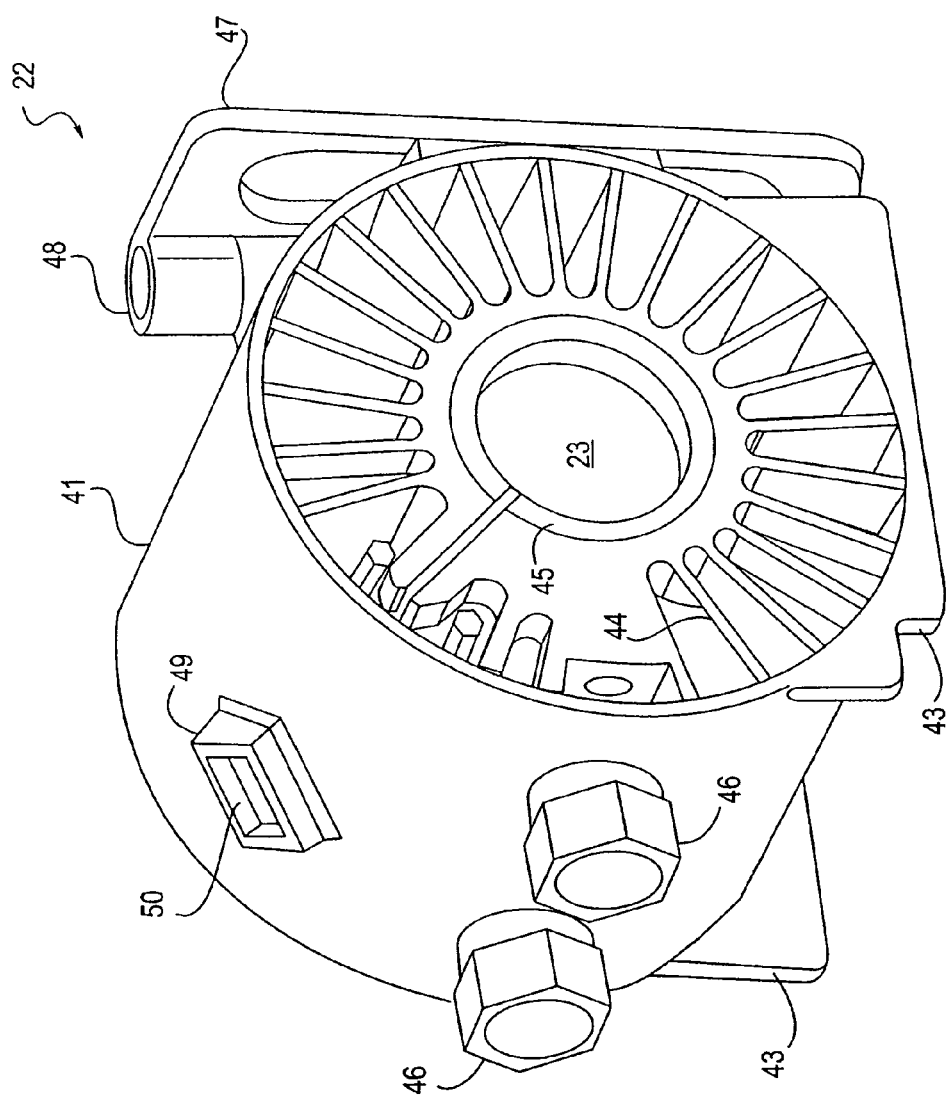
FIG. 4 is a perspective view of a light bulb assembly with an RFID tag affixed thereto.

FIG. 4 shows an embodiment of the light bulb assembly 22, illustrating how the RFID tag 27 can be affixed to it. The light bulb assembly 22 can be installed in the light source unit 21 has shown in FIG. 5. The light bulb assembly 22 includes a hollow cylindrical housing 41, a heat sink installed within the interior of the housing 41, and the light bulb 23, which is the light source of the light source unit 21. The housing 41 is made of plastic and includes two flat extensions 43 from the front and back of the lower portion of its exterior surface, which provide a stable base for the light bulb assembly 22. The heat sink comprises a hollow metal cylindrical hub 45 and a number of flat metal vanes 44 that extend radially from the hub 45 almost to the interior surface of the housing 41. The light bulb 23 is installed in the interior of the hub 45.

When the light bulb assembly 22 is installed in the light source unit 21, electrical terminals (not shown) of the light bulb 23 electrically connect to the power supply 30 via two socket connectors 46 on the light bulb assembly 22, which mate with two corresponding conductive prongs (terminals) on the power supply 30. The light bulb assembly 22 is removable from the light source unit 21 (e.g., for inspection or replacement) and includes a handle to facilitate removal. The handle 47 is mounted on a hinge 48 attached to the exterior of the housing 41. The light bulb assembly 22 is removed from the light source unit 21 by pulling on the handle 47, causing the light source assembly 22 to slide away from the power supply 30 so as to disconnect it from the power supply 30.

Figure 5:
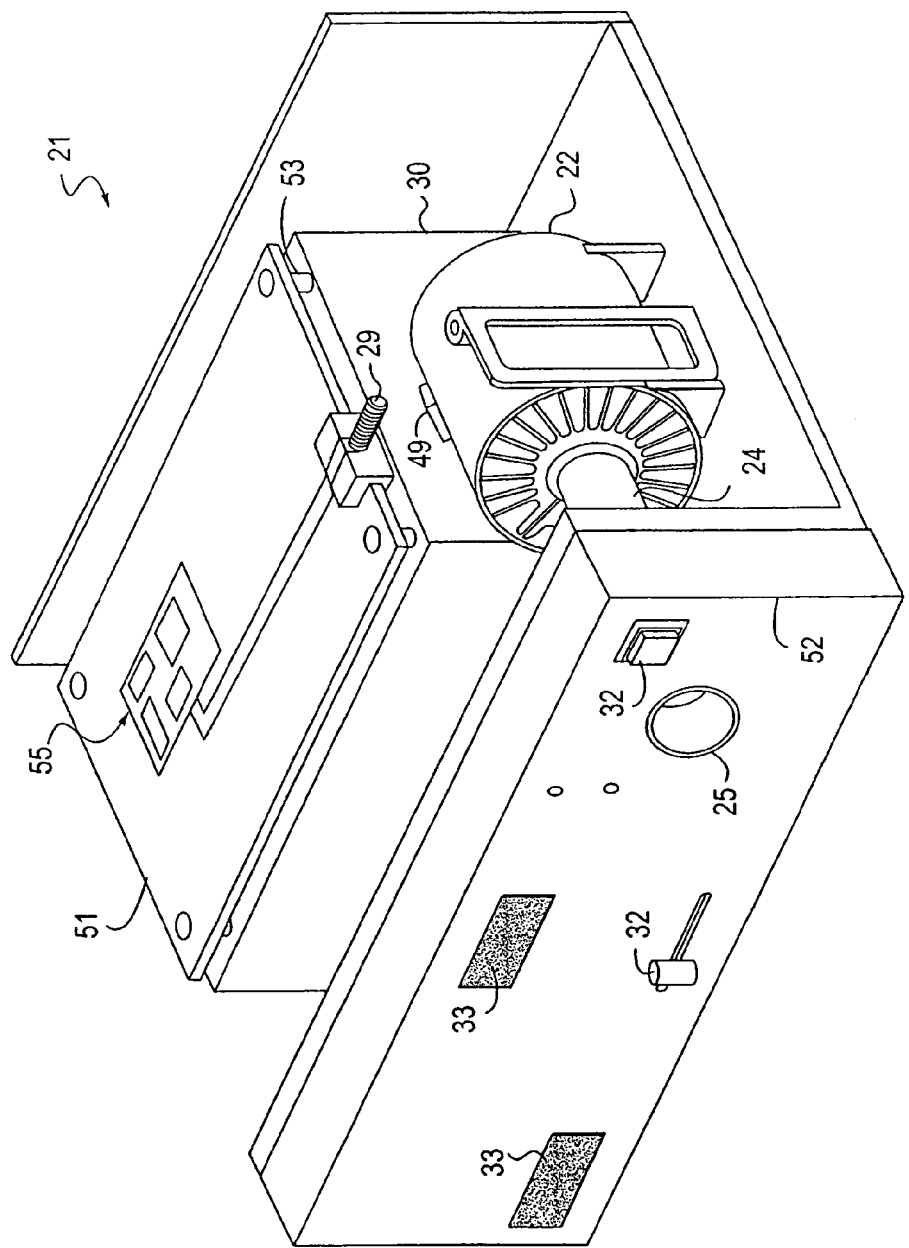
FIG. 5 is a perspective installation drawing of a light source unit for use in an endoscopic imaging system, including a light bulb assembly with an RFID tag affixed thereto.

To accommodate the RFID tag 27, the light bulb assembly 22 also includes small rectangular pedestal 49 on the upper portion of the exterior surface of the housing 41. The pedestal may be formed integrally with the exterior surface of the housing 41, or it may be manufactured as a separate component and then affixed to the exterior surface of the housing 41. As shown in FIG. 4, the pedestal 49 is located slightly offset from the top of the housing 41 (at about the "10 o'clock" position when viewing the light bulb end on), in order to provide the RFID tag 27 with an optimum position and orientation relative to the antenna 29, as shown in FIG. 5. In other embodiments, different positions and orientations of the antenna 29 and pedestal 49 may be used.

The RFID tag 27 is typically embodied as a conventionally packaged microelectronic chip. During manufacture of the light bulb assembly 22, the RFID tag is placed within a shallow depression 50 at the top of the pedestal 49. The RFID tag 27 is then fixed in this position by applying a layer of glue (e.g., epoxy) over it, which completely encases the RFID tag 27 and fixes it to the housing 41 when the glue is hardened/cured. Once hardened/cured, the glue serves both to fix the RFID tag 27 to the housing 41 and to protect the RFID tag 27 from damage and tampering.

FIG. 5 shows how the light bulb assembly 22 can be installed in the light source unit 21, to allow wireless communication between the RF transceiver 28 and the RFID tag 27. More specifically, FIG. 5 shows a perspective view of the light source unit 21, with its cover removed so as to expose certain internal components, including the light bulb assembly 22, the power supply 30, and a circuit board 51. The light source unit 21 has a front panel 52 that provides a user interface, including the input controls 32, the output devices 33, and the light conduit connector 25. One of the output devices 33 (an LCD, for example) is used to display light bulb usage hours. Other conventional and well-known components of the light source unit 21 which are not germane to the present invention are not shown in FIG. 5.

Figure 6:
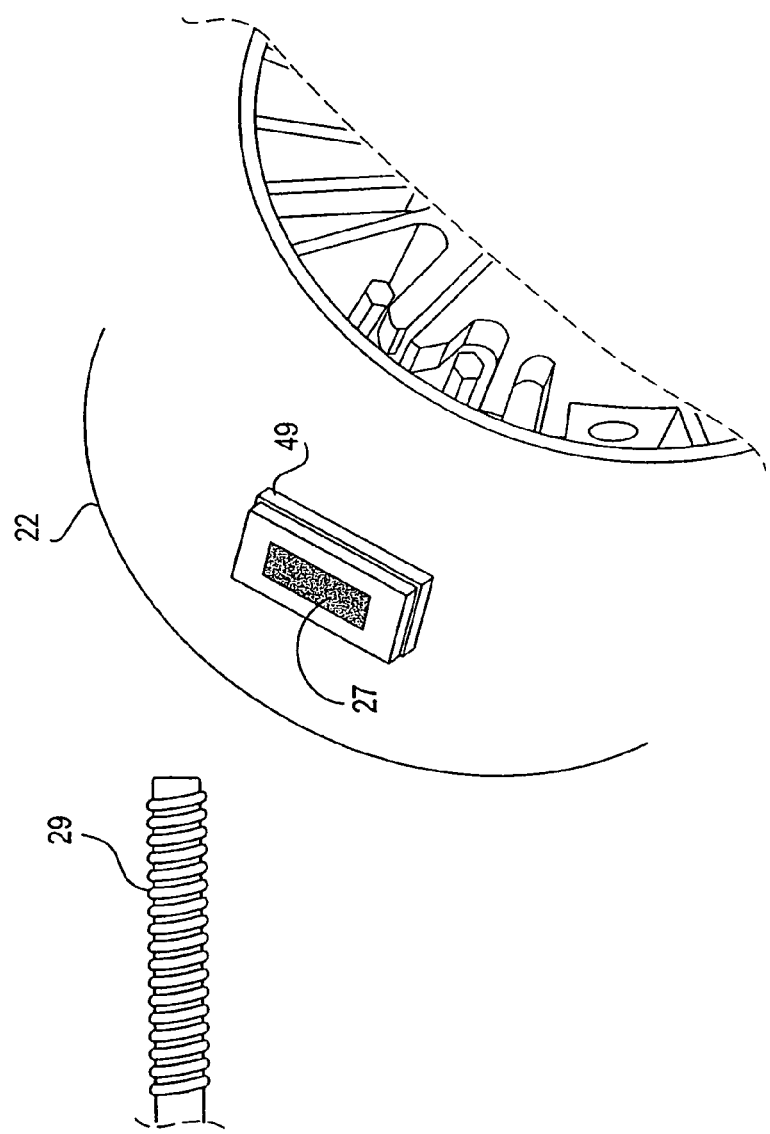
FIG. 6 is close-up view showing the relative position and orientation of the antenna and the RFID tag.

The light bulb assembly 22 is electrically connected to the power supply 30 and is installed adjacent to the power supply 30, such that the light bulb 23 is optically aligned with the optical coupler 24. The circuit board 51 is mounted on top of the power supply 30 and is raised above the top surface of the power supply 30 by spacers 53 to facilitate heat dissipation. Mounted on the circuit board 51 are the antenna 29 and a set of microelectronic devices 55, which may include the RF transceiver 28, the microcontroller 26, the timer 31, memory 38 and network adapter 39 (see FIG. 2). The antenna 29 extends horizontally beyond the edge of the circuit board 51 in a position such that the center of the antenna 29 is about one inch from the center of the RFID tag 27 mounted on the light bulb assembly 22, when the light bulb assembly 22 is installed in the light source unit 21. FIG. 6 is a close-up view showing the relative position and orientation of the antenna 29 and the RFID tag 27.

When the light bulb assembly 22 is manufactured, an initial value representing bulb usage hours is stored in the memory 37 (see FIG. 3) within the RFID tag 27. Since the manufacturer of the light bulb assembly 22 is not necessarily the manufacturer of the whole light source unit 21, this process of storing the initial value may be done using transceiver circuitry that is similar to that shown in FIG. 2 but not necessarily part of a light source unit 21. The initial value will normally be zero or a small non-zero value to reflect the manufacturer's testing of the light bulb 23.

When the fully assembled light source unit 21 is powered on, the microcontroller 26 causes the RF transceiver to read the value of bulb usage hours stored in the RFID tag 27. The RF transceiver 28 passes the value to the microcontroller 26, which causes one of the output devices 33 (e.g., an LCD) to display to the user an indication of the cumulative duration of use of the light bulb. The microcontroller 26 keeps track of further bulb use based on timing input from the timer 31. Periodically (e.g., once per minute), the microcontroller 26 causes the RF transceiver 28 to update (rewrite) the value stored in the RFID tag 27 to reflect further use of the light bulb, and the output indication to the user is updated accordingly.

Besides bulb usage hours, other types of information may also be stored in the memory 37 within the RFID tag 27, such as a password or other authentication data (which can be used to protect the light source unit from external interruptions for intrusions), user preferences, usage logs, error logs, device settings, current software version, etc. A password, for example, may be used to selectively enable or disable use of the light source unit. As another example, the RFID tag 27 may store data identifying the light bulb 23 or the light bulb assembly 22, (e.g., by manufacturer, model number and serial number). As yet another example, the microcontroller 26 may be configured to cause the RF transceiver 28 to store in the RFID tag 27 data identifying the light source unit 21 (e.g., by manufacturer, model number and serial number). This data could then be used, for example, by the manufacturer to determine whether the light bulb assembly 22 has been used improperly in a light source unit for which it is not qualified or compatible, if the light bulb assembly 22 (or the entire light source unit 21) requires service after a failure. The memory 37 in the RFID tag 27 can also be used to store performance data relating to any one or more components in the light source unit 21 (which may include diagnostic data relating to operation or failure of the component), which is not limited to the light bulb 23 or the light bulb assembly 22. This data can be used by the manufacturer to provide better service and to improve future product designs. Thus, essentially any kind of data can be stored in the RFID tag 27. In general, after the initial data is set in the RF ID tag 27 by the manufacturer, the microcontroller 26 determines what data is stored in and read from the RFID tag 27 and when such data is stored or read, according to its programming.

Figure 7:
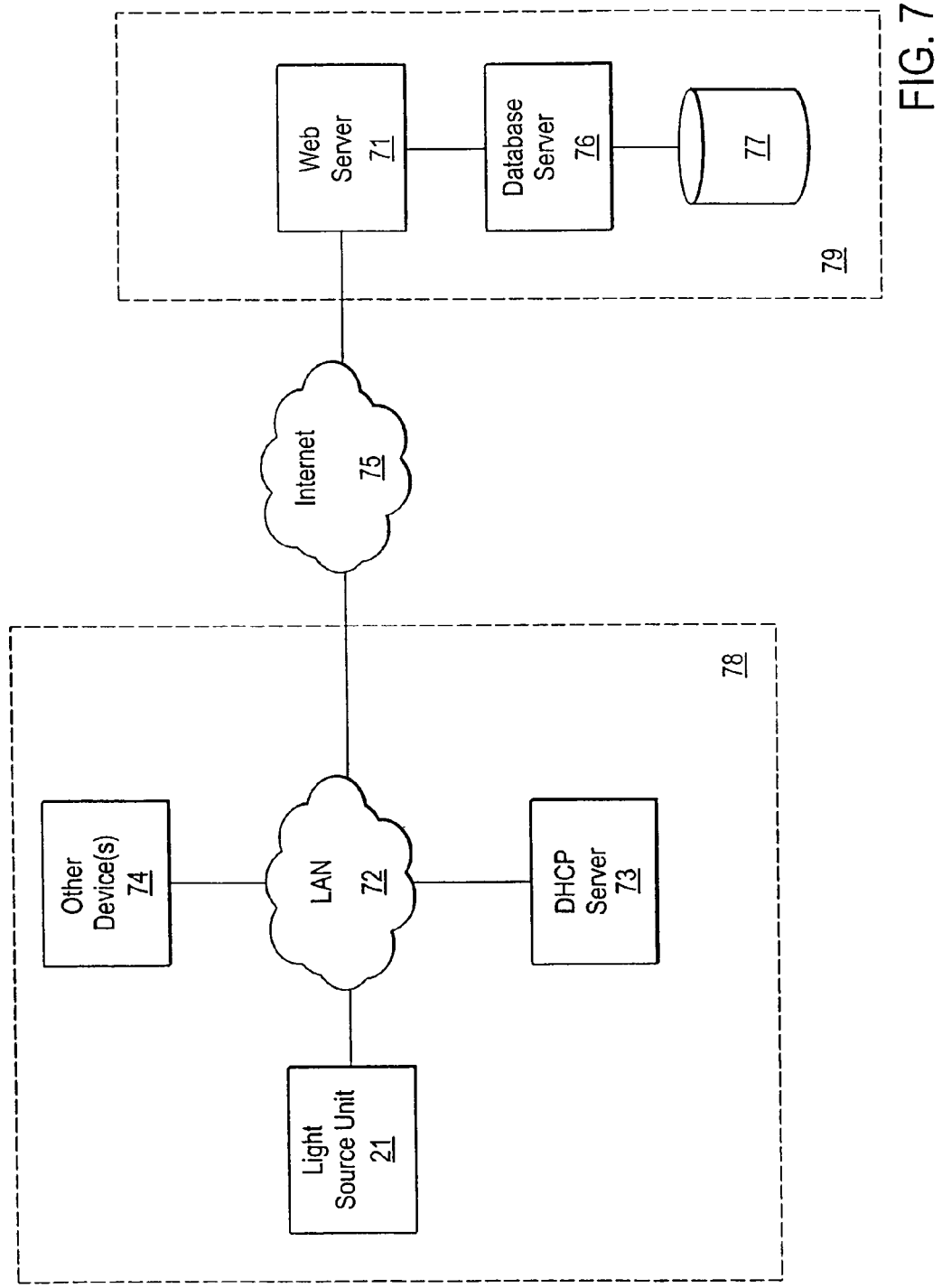
FIG. 7 shows a network configuration in which the light source unit is connected to a remote server at a manufacturer site through various networks.

FIG. 7 shows a network configuration in which the light source unit 21 is connected to a remote web server at a manufacturer site through various networks. In the illustrated embodiment, the light source unit 21 is connected via a LAN 72 to a dynamic host configuration protocol (DHCP) server 73 and to various other devices 74 (such as one or more personal computers, servers, or medical instruments), all located within a hospital's premises 78. The LAN 72 is connected via the Internet 75 to a remote web server 71 at the manufacturer's premises 79. Of course, in other embodiments, the remote web server 71, database server 76 and/or the database 77 may be operated by a third party and/or located at a third party's premises. The web server 71 is also connected to a database server 76, which provides the web server 71 with access to a database 77. In other embodiments, the Internet 75 and/or the LAN 72 may be replaced by a different type of network or networks.

As described further below, information of various types can be sent automatically from the light source 21 unit to the manufacturer's web server 71. The information may include, for example, device settings, user preferences, usage logs, error logs, light bulb hours, current software version, and/or essentially any other type of information relating to, or acquired by, the light source unit. In certain embodiments, the information is communicated between the light source unit 21 and the web server 71 by using active server pages (ASPs). For example, data may be uploaded to the web server 71 using an HTTP POST which refers to an ASP. The information may be sent in ASCII and hexadecimal format. The specific format and content of such ASPs are implementation-specific and, therefore, need not be described herein.

The manufacturer may choose to store at least some of the data uploaded from the light source unit 21 in the database 71, using the database server 76. In addition, using this network configuration the manufacturer can download software upgrades (including any necessary "patches") to the light source unit 21 when they become available.

Figure 8:
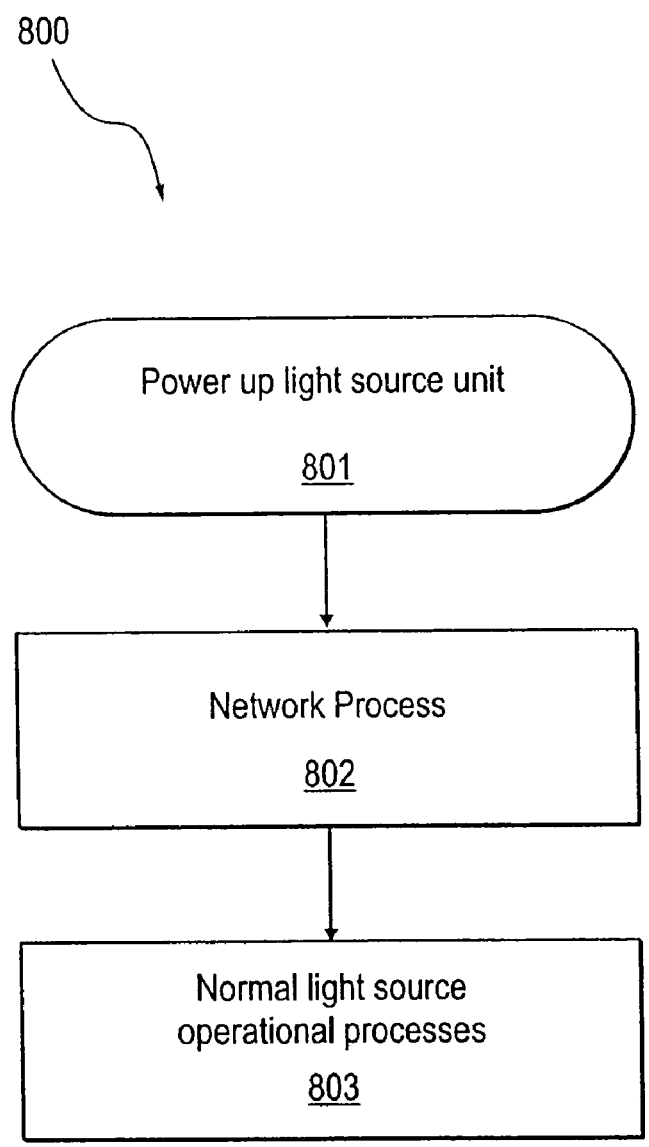
FIG. 8 shows the overall process performed by the light source unit according to certain embodiments of the invention.

In certain embodiments, as illustrated in FIG. 8, the light source unit 21 automatically runs its network process 802 immediately in response to power up 801 of the light source unit. The network process 802 includes attempting to establish a network connection with the remote web server 71 and, if successful, sending certain data to the web server 71 (e.g., by sending ASP units), as described further below with reference to FIG. 9. After completion of the network process 802, the light source unit 21 enables and runs its normal operational processes 803 (i.e., the processes directly related to use of the light source). Thus, the network process 802 can be considered part of an initialization process of the light source unit 21.

Figure 9:
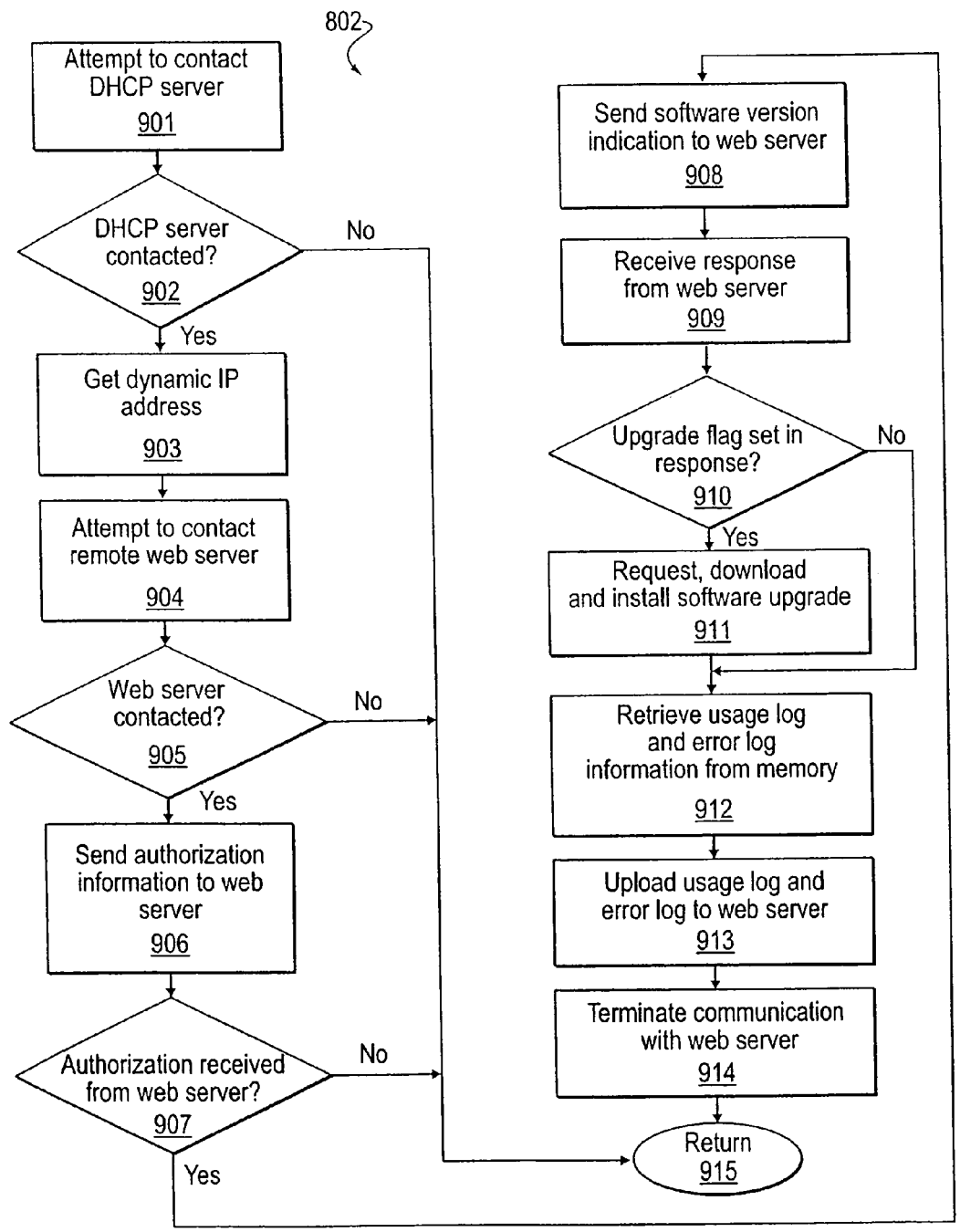
FIG. 9 shows the network process performed by the light source unit according to certain embodiments of the invention.

FIG. 9 shows the network process 802 in the light source unit according to certain embodiments of the invention, which may be implemented in conjunction with the network configuration of FIG. 7. In general, the network process 802 is controlled cooperatively by the microcontroller 26 and the network adapter 39. Portions of the process may be performed by the microcontroller 26 while other portions of the process are performed by the network adapter 39, as will be readily apparent to those skilled in the art.

Initially, at 901 the light source unit 21 attempts to contact the DHCP server 73. If the attempt is unsuccessful, then at 915 the network process 801 returns to the main process 800 (FIG. 8). If the attempt is successful, then at 903 the light source unit 21 gets a dynamic Internet Protocol (IP) address from the DHCP server 73. The light source unit 21 then attempts to contact the manufacturer's web server 71 at 904. If this attempt is unsuccessful, then the network process 802 returns to the main process 800 at 915. If the attempt is successful, then at 906 the light source unit 21 sends authorization information to the web server 71, to request an authorization.

In certain embodiments, the authorization may be used only to authorize the exchange of information between the light source unit and the web server, as assumed herein. In other embodiments, however, the authorization may be to enable or disable operation of the entire light source unit 21. The authorization information sent by the light source unit 21 may include, for example, a serial number and/or password associated with the light bulb assembly 22 or the light source unit 21, or other information.

If the response to the authorization information from the web server 71 includes an authorization at 907, then the network process 802 continues at 908. Otherwise, the network process 802 returns to the main process 800 at 915.

At 908 the light source unit 21 sends the web server 21 an indication of the version of software currently installed within the light source unit 21, and a corresponding response from the web server 71 is received at 909. The light source unit 21 then determines at 910 whether an upgrade flag is set in the response. The upgrade flag is a result of a determination, made by the web server 71, of whether the light source unit 21 has the most recent software version, based on the version indication sent by the light source unit 21. If the upgrade flag is set in the response from the web server 71, the light source unit 21 requests, downloads, and installs a software upgrade from the web server 71 (or such other source as may be indicated in the response), and the network process 802 then continues at 912. If the upgrade flag was not set in the response, then the network process 802 jumps from 910 directly to 912.

At 912 the light source unit 21 retrieves usage logs and error log information from memory and then uploads this information to the web server 71 at 913. Other types of information may also be retrieved and uploaded to the web server 71 at 912 and 913, respectively. The retrieval of information from memory at 912 may involve retrieving at least some of the information from the RFID tag 27, while other information may be retrieved from memory 38. After all of the information has been uploaded to the web server 71, at 914 the light source unit 21 terminates communication with the web server 71, and the network process 802 then returns at 915 to the main process 800.

As noted above, in other embodiments the features and functionality described above can be implemented in a unit of equipment other than a light source unit, such as an endoscopic camera control unit (CCU), an RF cutter console to control an RF cutter during endoscopic surgery, a shaver console to control a shaver during endoscopic surgery, or a footswitch console containing foot-operated switches to control the functionality of other endoscopic devices during endoscopic surgery.

Thus, to enable an endoscopy device with integral RFID capability to communicate with a remote server over a network have been described. Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. A method of operating an endoscopy device containing at least one replaceable component, comprising the steps of:
    storing information concerning the replaceable component into a non-volatile memory of an RFID tag located upon or incorporated within the replaceable component;
    establishing a wireless link between the RFID tag and an RFID tag transceiver disposed in the endoscopy device;
    retrieving the information stored in the RFID tag via the wireless link;
    establishing a data communication link between the endoscopy device and a remote server via a network; and
    conveying the retrieved information concerning the replaceable component from the endoscopy device to the remote server over the network.

2. The method according to claim 1, wherein the endoscopy device comprises one of an endoscopic camera control unit connected to a camera that is coupled to an endoscope, a RF cutter control console connected to an RF cutter, and a shaver control console connected to a shaver.

3. The method according to claim 1, wherein the replaceable component comprises a replaceable light source having the RFID tag located upon or incorporated within the light source, and wherein the endoscopy device comprises a light source unit for receiving the replaceable light source.

4. The method according to claim 1, including the step of storing code in a memory disposed in the endoscopy device for execution by a processor disposed in the endoscopy device.

5. The method according to claim 4, wherein the step of storing information comprises storing component usage data including at least one of cumulative time of activation data, usage log data, and error log data.

6. The method according to claim 1, further comprising the step of storing information concerning the endoscopy device in the RFID tag.

7. The method according to claim 1, wherein the step of retrieving the information in the RFID tag comprises retrieving the information in the RFID tag via the wireless link using a processor disposed in the endoscopy device.

8. The method according to claim 1, wherein the steps of establishing a wireless link, retrieving information stored in the RFID tag, establishing a data communication link, and conveying the retrieved information all occur automatically in response to the endoscopy device powering up.

9. The method according to claim 1, wherein the remote server is operated by a manufacturer of the endoscopy device.

10. A method of operating an endoscopy device containing at least one replaceable component, comprising the steps of:
storing information concerning at least one of the replaceable component and information concerning the endoscopy device comprising at least one of device settings, a device usage log, a device error log, device authentication data, user preferences, and version of software installed in the device into a non-volatile memory of a RFID tag located upon or incorporated within the replaceable component;
establishing a wireless link between the RFID tag and a RFID tag transceiver disposed in the endoscopy device;
retrieving via the wireless link the information concerning at least one of the endoscopy device and the replaceable component that is stored in the RFID tag;
establishing a data communication link between the endoscopy device and a remote server via an external network; and
conveying the retrieved information concerning at least one of the endoscopy device and the replaceable component from the endoscopy device to the remote server over the external network.

11. The method according to claim 10, further comprising the steps of:
checking via the data communication link whether an updated version of the software installed in the endoscopy device is available from the remote server;
retrieving the updated version of the software from the remote server; and
installing the updated version of the software in the endoscopy device.

12. The method according to claim 10, wherein the steps of establishing a wireless link, retrieving via wireless link information stored in the RFID tag, establishing a data communication link, and conveying the retrieved information all occur automatically in response to the endoscopy device powering up.

13. The method according to claim 10, wherein the step of conveying comprises conveying the retrieved information to the remote server over at least one of a local area network, a wide area network, and the Internet.

14. The method according to claim 10, wherein the remote server is operated by a manufacturer of the endoscopy device.

15. The method according to claim 10, wherein the step of retrieving via the wireless link the information concerning at least one of the endoscopy device and the replaceable component that is stored in the RFID tag comprises retrieving the information via the wireless link using a processor disposed in the endoscopy device.

16. The method according to claim 15, including storing code in a memory disposed in the endoscopy device for execution by the processor.

17. The method according to claim 10, wherein the replaceable component comprises a replaceable light source having the RFID tag located upon or incorporated within the light source, and wherein the endoscopy device comprises a light source unit for receiving the replaceable light source.

18. A method of operating an endoscopy device containing at least one replaceable component, comprising the steps of:
storing usage data concerning the replaceable component into a non-volatile memory of an RFID tag located upon or incorporated within the replaceable component;
tracking usage of the replaceable component with a processor and a RFID tag transceiver disposed in the endoscopy device;
establishing a wireless link between the RFID tag and the RFID tag transceiver disposed in the endoscopy device;
updating the usage data stored in the RFID tag via the wireless link at least once during operation of the endoscopy device;
retrieving the usage data stored in the RFID tag via the wireless link;
establishing a data communication link between the endoscopy device and a remote server via a network; and
conveying the retrieved usage data concerning the replaceable component from the endoscopy device to the remote server over the network.

19. The method according to claim 18, including the step of storing code for execution by the processor in a memory disposed in the endoscopy device.

20. The method according to claim 18, wherein the replaceable component comprises a replaceable light source having the RFID tag located upon or incorporated within the light source, and wherein the endoscopy device comprises a light source unit for receiving the replaceable light source.

* * * * *